United States Patent
Li et al.

(10) Patent No.: US 10,519,157 B2
(45) Date of Patent: Dec. 31, 2019

(54) DEUTERATED COMPOUNDS FOR TREATING FABRY, GAUCHER, PARKINSON'S AND RELATED DISEASES AND CONDITIONS, AND COMPOSITIONS AND METHODS THEREOF

(71) Applicant: X-Cutag Therapeutics, Inc., Framingham, MA (US)

(72) Inventors: Hui Joyce Li, Westborough, MA (US); Shuhao Wen, Andover, MA (US); Changfu Cheng, Northborough, MA (US); Xiao Chen, Princeton, NJ (US); Gao Shang, Doylestown, PA (US)

(73) Assignee: X-CUTAG THERAPEUTICS, INC., Framingham, MA (US)

( * ) Notice: Subject to any disclaimer, the term of this patent is extended or adjusted under 35 U.S.C. 154(b) by 0 days.

(21) Appl. No.: 16/270,728

(22) Filed: Feb. 8, 2019

(65) Prior Publication Data

US 2019/0248790 A1    Aug. 15, 2019

Related U.S. Application Data

(60) Provisional application No. 62/628,458, filed on Feb. 9, 2018.

(51) Int. Cl.
| | |
|---|---|
| *C07D 453/00* | (2006.01) |
| *A61K 31/439* | (2006.01) |
| *C07D 471/08* | (2006.01) |

(52) U.S. Cl.
CPC ........ *C07D 471/08* (2013.01); *C07B 2200/05* (2013.01)

(58) Field of Classification Search
CPC .......................... C07D 453/00; A61K 31/439
USPC .......................................................... 546/112
See application file for complete search history.

(56) References Cited

U.S. PATENT DOCUMENTS

| | | | | |
|---|---|---|---|---|
| 9,139,580 | B2 * | 9/2015 | Bourque | A61K 31/439 |
| 9,518,049 | B2 * | 12/2016 | Siegel | C07C 59/245 |
| 9,682,975 | B2 * | 6/2017 | Siegel | C07D 417/06 |

OTHER PUBLICATIONS

Tung et al., The Development of Deuterium-Containing Drugs, Innovations in Pharmaceutical Technology, issue 32, (2010), pp. 1-4.*

* cited by examiner

*Primary Examiner* — Niloofar Rahmani
(74) *Attorney, Agent, or Firm* — Wenderoth, Lind & Ponack L.L.P.

(57) ABSTRACT

Novel deuterium-containing chemical compounds are provided. They are glucosylceramide (GSC) synthase inhibitors and are useful for treating various types of lysosomal storage diseases including Fabry's disease, Gaucher's disease and Parkinson's disease, or related diseases and conditions. Also described are pharmaceutical compositions, and methods of preparation and use thereof.

3 Claims, 9 Drawing Sheets

Figure 1a. Mass spectrometric analysis of ibiglustat: Full-scan spectrum
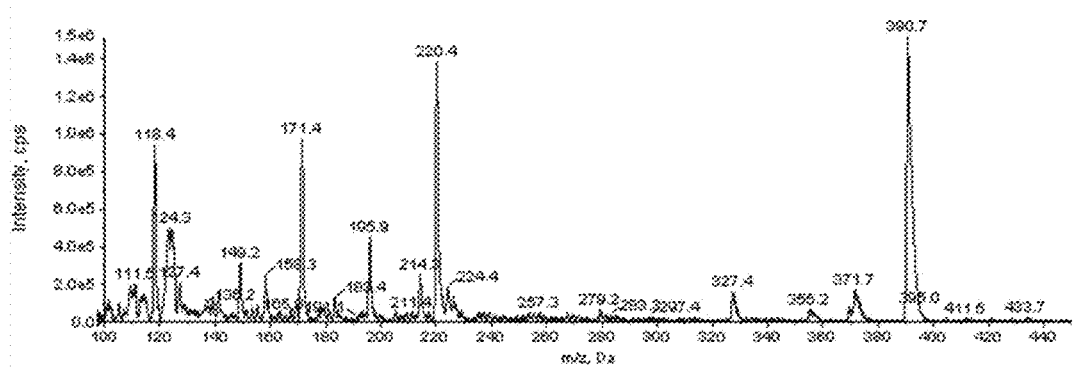
Figure 1b. Mass spectrometric analysis of ibiglustat: Product-ion scan spectrum
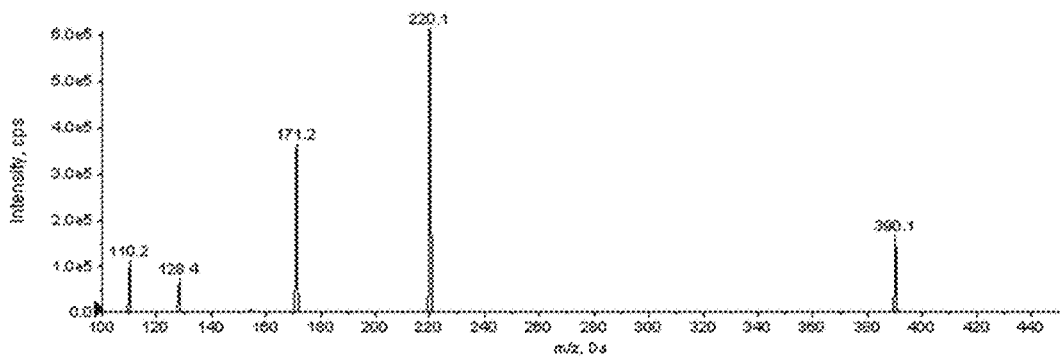

Figure 2a. Mass spectrometric analysis of compound 1 (ibiglustat-d6): Full-scan spectrum
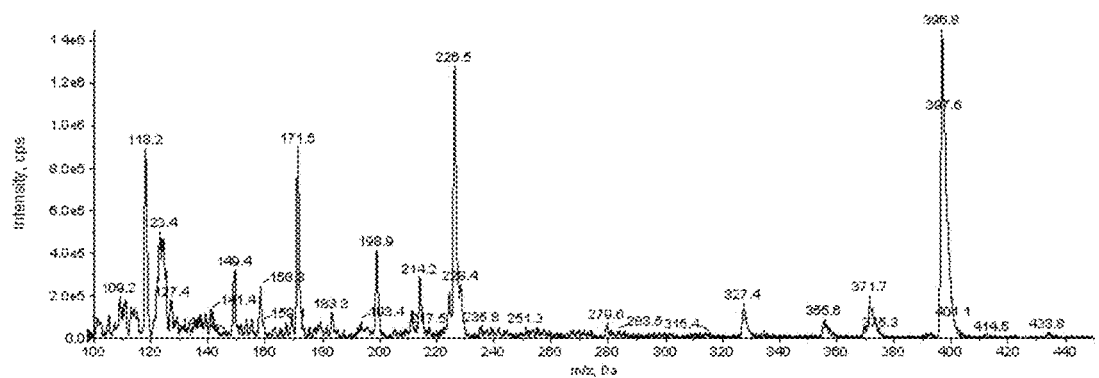
Figure 2b. Mass spectrometric analysis of compound 1 (ibiglustat-d6): Product-ion scan spectrum.
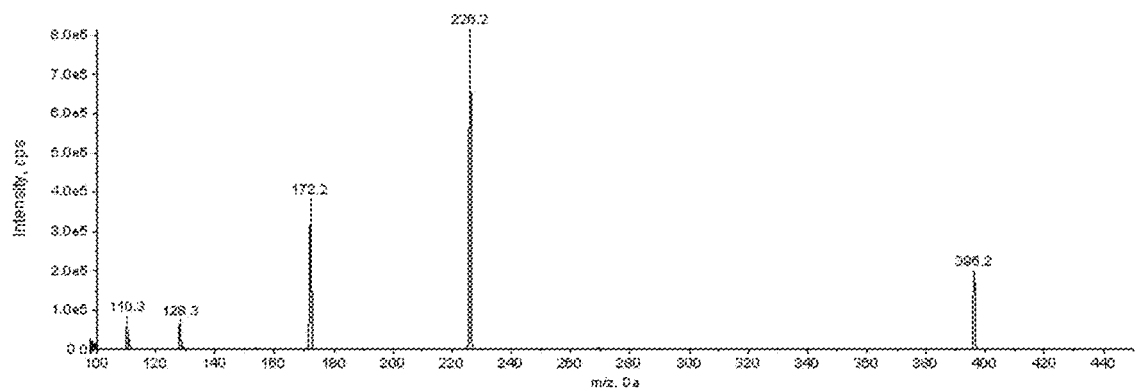

Figure 3a. Mass spectrometric analysis of compound 1b (ibiglustat-d12): Full-scan spectrum
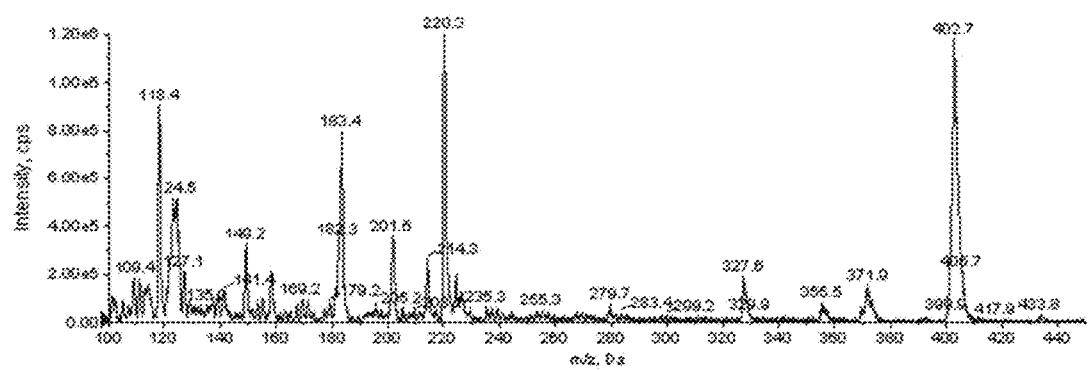
Figure 3b. Mass spectrometric analysis of compound 1b (ibiglustat-d12): Product-ion scan spectrum.
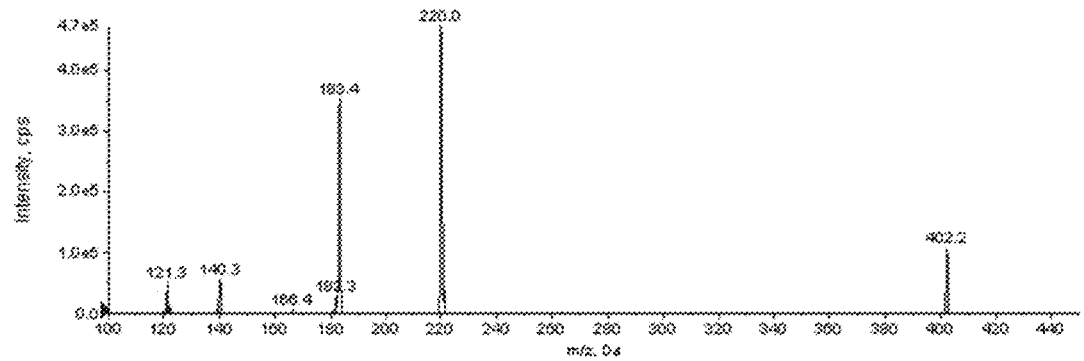

Figure 4a. Mass spectrometric analysis of compound 1a (ibiglustat-d18): Full-scan spectrum
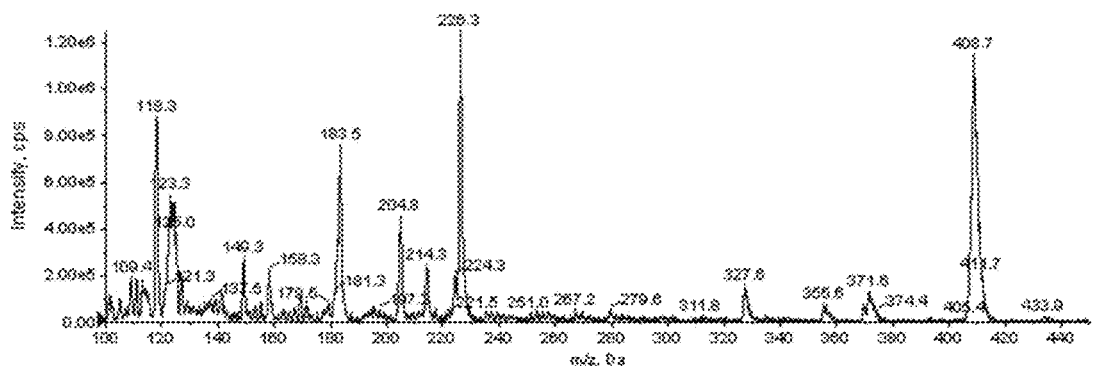
Figure 4b. Mass spectrometric analysis of compound 1a (ibiglustat-d18): Product-ion scan spectrum
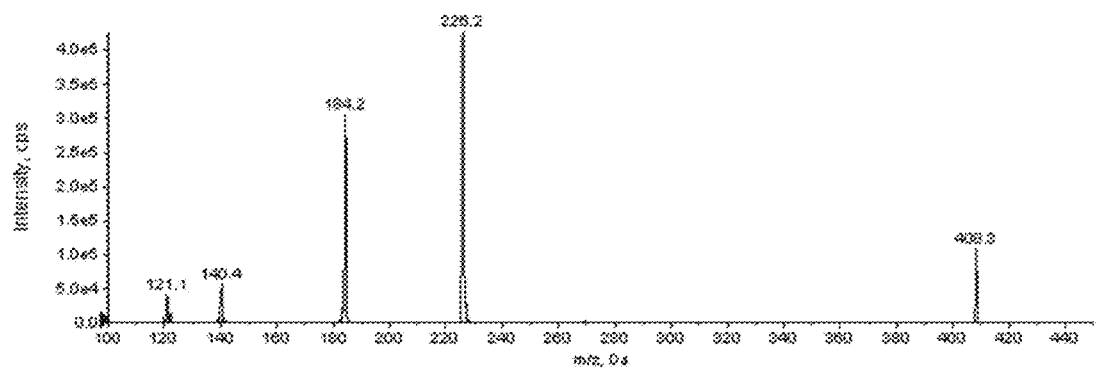

Figure 5. Exemplary NMR spectrum of compounds in the invention (compound 1, ibiglustat-d6).
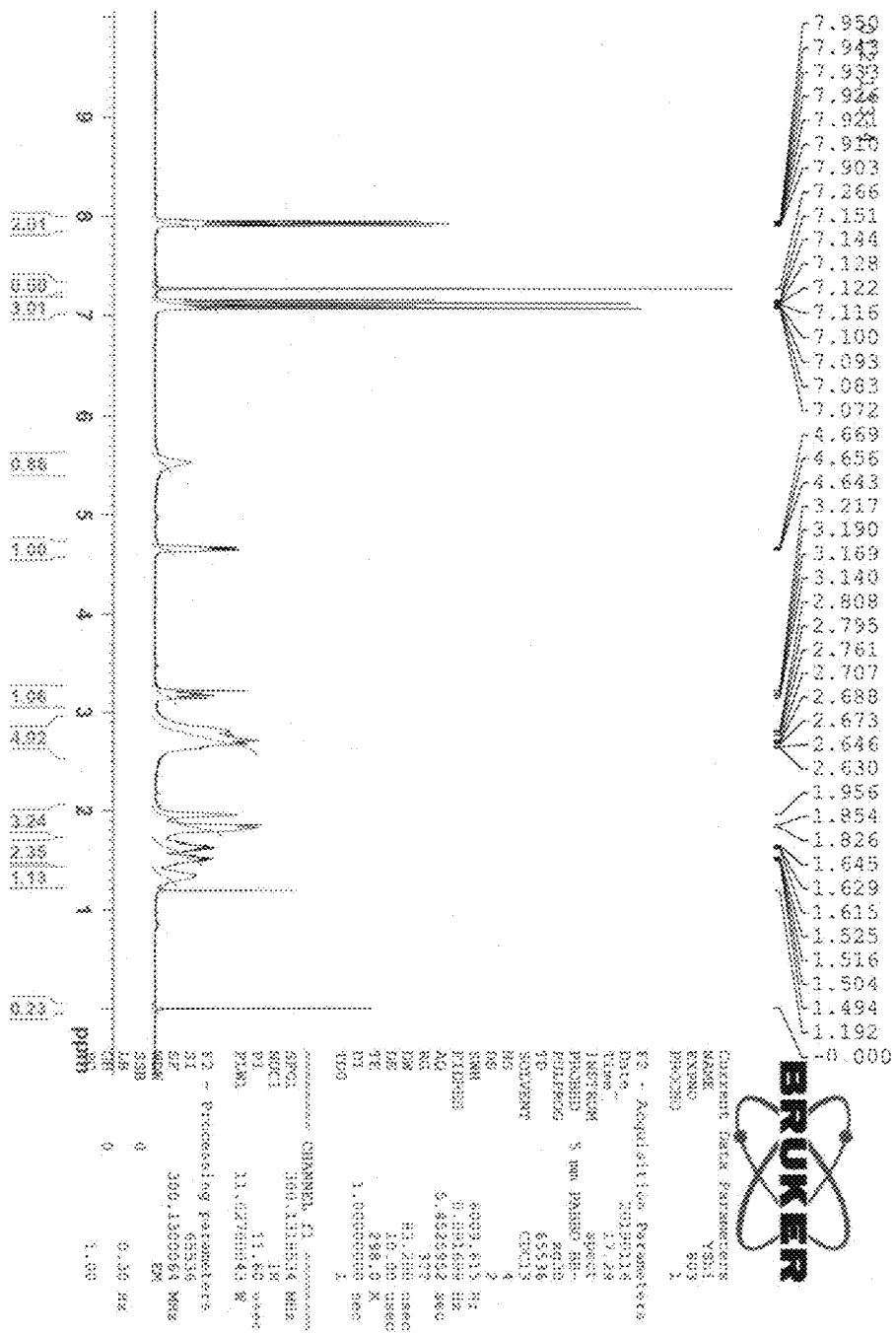

Figure 6. Exemplary NMR spectrum of compounds in the invention (compound 1a, ibiglustat-d18).
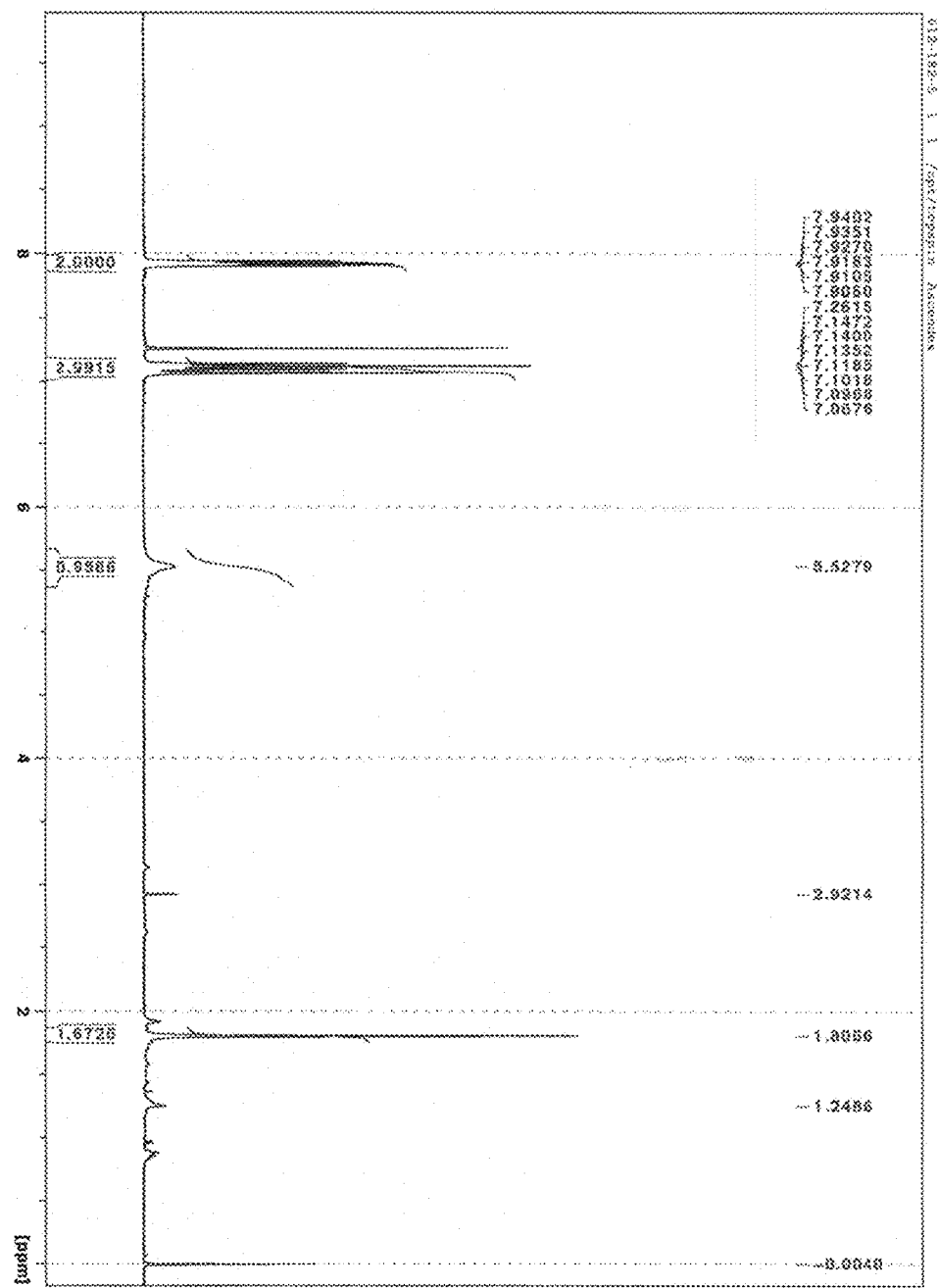

Figure 7. Exemplary NMR spectrum of compounds in the invention (compound 1b, ibiglustat-d12).
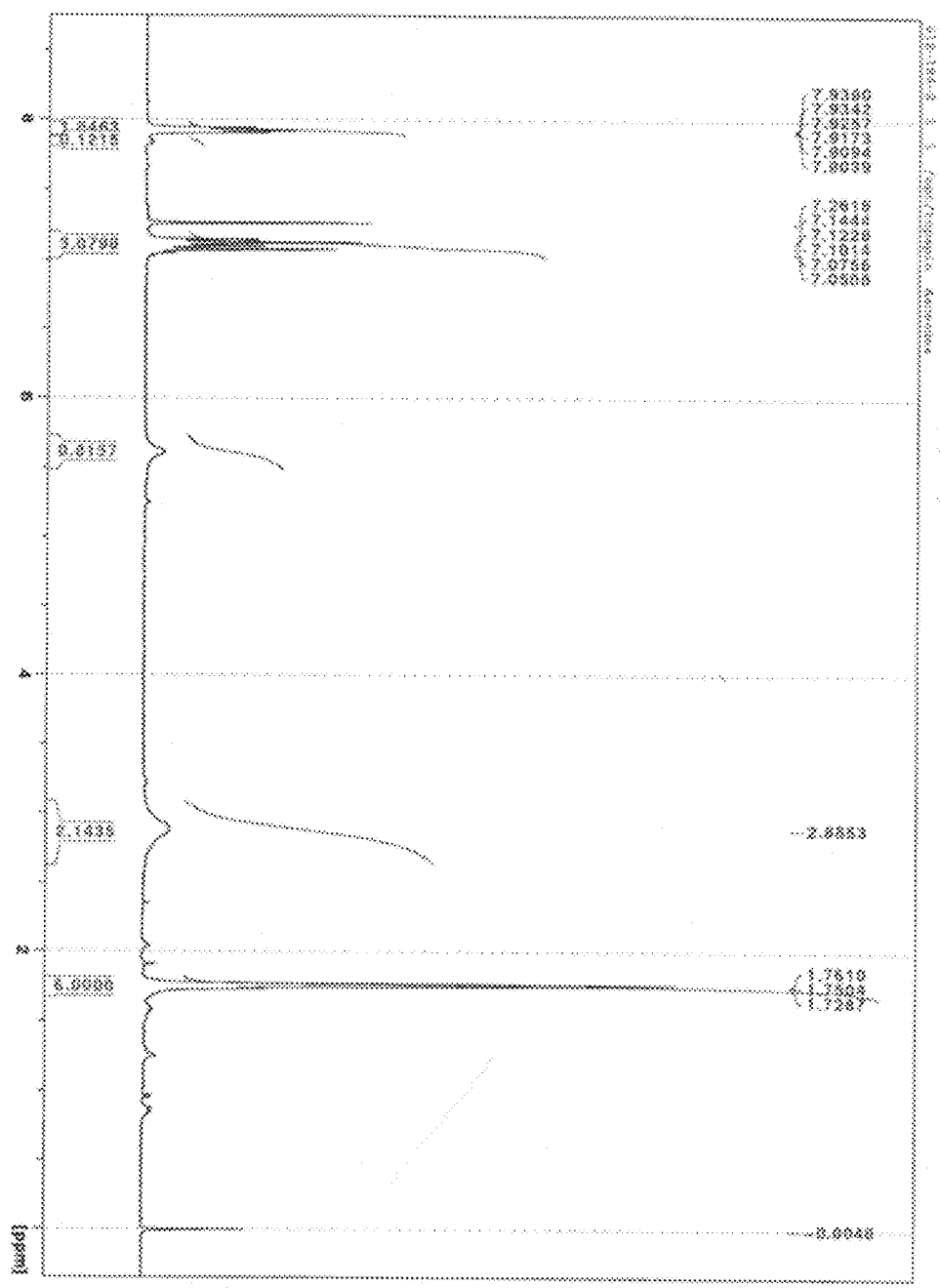

Figure 8. Exemplary results of ibiglustat vs. compounds in the invention when co-incubated in rat microsomes
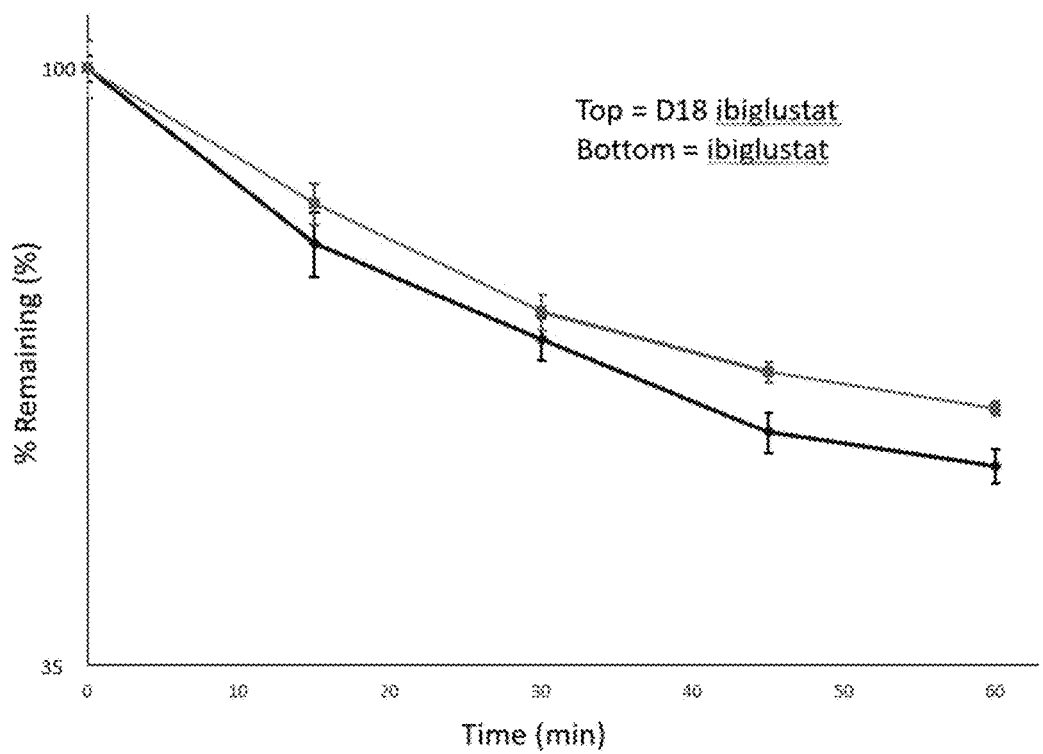

Figure 9. Exemplary results of ibiglustat vs. compounds in the invention when co-incubated in dog microsomes
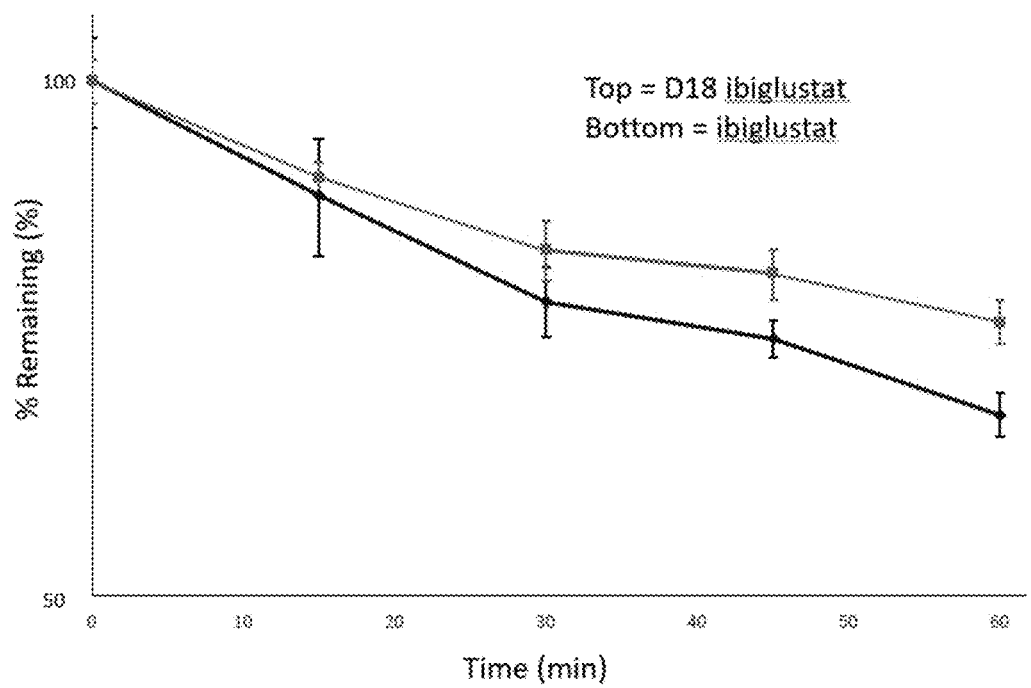

DEUTERATED COMPOUNDS FOR TREATING FABRY, GAUCHER, PARKINSON'S AND RELATED DISEASES AND CONDITIONS, AND COMPOSITIONS AND METHODS THEREOF

TECHNICAL FIELD

The invention generally relates to therapeutics and treatment methods for certain diseases and conditions. Specifically, this invention provides novel chemical compounds, including [(3S)-1-azabicyclo[2.2.2]octan-3-yl]N-[2-[2-(4-fluorophenyl)-1,3-thiazol-4-yl]propan-2-yl]carbamate (also known as ibiglustat) with one or more deuterium-substitutions at strategic positions. These compounds are glucosylceramide (GSC) synthase inhibitors, useful for treating various types of lysosomal storage diseases including Fabry's disease, Gaucher's disease and Parkinson's disease, or related diseases and conditions. The invention further relates to pharmaceutical compositions and methods of preparation and use thereof.

BACKGROUND OF INVENTION

Lysosomal storage diseases (LSDs) are a group of over 60 different rare, inherited metabolic diseases caused by gene mutations that impair lysosomal function and homeostasis (Schultz et al. 2011; Lieberman et al. 2012). They typically present in childhood, collectively affecting 1 in 7,000 live births, of which most are fatal at young age. Lysosomes are membrane-enclosed acidic cytoplasmic organelles that contain about 60 specialized acid hydrolases to break down all types of biological macromolecules (aka cellular waste) including proteins, nucleic acids, lipids and carbohydrates (Saftig 2006). Genetic mutations of genes encoding lysosomal enzymes such as hydrolases or associated proteins cause blockages in stepwise degradations of those cellular macromolecules (substrates), leading to their accumulation or partial accumulation in the lysosomes. The intra-lysosomal accumulation of non-degraded substrates will affect multiple tissue and organ systems including brain, bone, heart and viscera. Early onset central nervous system dysfunction predominates most of LSDs, with various progressive clinical phenotypes. All LSDs are recessively inherited monogenic disorders, and a few are X-linked inheritance such as Fabry and Hunter diseases (Desnick et al. 2003; de Camargo Pinto et al. 2011).

LSDs can be categorized based on the type of macromolecules (lipid, mucopolysaccharidoses, glycoprotein, etc.) that fail to be degraded and are consequently stored (Schultz et al. 2011). Sphingolipids are one type of lipid macromolecules that play significant roles in cell signaling, and regulate cell function through their bioactive metabolites. The synthesis and degradation of sphingolipids are governed by a cascade of enzymatic reactions in common synthetic (in ER) and catabolic (in lysosomes) pathways. Three major rate limiting enzymes in sphingolipid biosynthesis are ceramide galactosyltransferase (CGT), glucosylceramide synthase (GCS) and sphingomyelin synthase (Gault, Obeid, and Hannun 2010). They generate precursors from ceramide for galactosphingolipids, glucosphigolipids and sphingomyelin, respectively, in ER and Golgi compartments. Glucosylceramide is the precursor for majority of all glycosphingolipids that are essential for cell-cell recognition during development. On the other hand, those complex sphingolipids are constantly catabolized into ceramide for recycling and preventing lipid accumulation in the cells that are toxic to proper cell functions. Glycosphinolipid hydrolases are needed for glycosphingolipid catabolism. Mutations of genes encoding those glycohydrolases including glucocerebrosidase (GBA1) and alpha-galactosidase A (GLA) are the mechanisms underlying most common lipid storage diseases.

Gaucher and Fabry diseases carrying mutations on GBA1 and GLA, respectively, represent the prototypic sphingolipid storage disorders. Gaucher disease is the most common lysosomal storage disease with incidence of 1 in 40,000 for non-Jewish population. It is an autosomal recessive disorder caused by mutations in the GBA1 gene. GBA1 encodes for beta-glucocerebrosidase that degrades glucosylceramide to ceramide and glucose (Mistry et al. 2017). Its deficiency causes accumulation of glucoceramide in macrophages of the spleen, liver, bone marrow and lung. Patients suffer from significant anemia, bone lesion, hepatosplenomegaly, thrombocytopenia and growth retardation. Most of the Gaucher disease alleles are GBA missense mutations that lead to the synthesis of acid beta-glucosidases with decreased catalytic function and/or stability; whereas nonsense/frameshift mutations in GBA genes have also been reported. GBA mutations are also strong risk factors for neurologic disorders like Parkinson disease (PD) and Dementia with Lewy bodies (DLB), with 2.3-9.4% of PD patients carrying a GBA mutation (Balestrino and Schapira 2018). Fabry disease, on the other hand, is an X-linked sphinogolipid storage disease due to the loss (majority cases) of alpha-galactosidase activity (Chan and Adam 2018). Its prevalence ranges from 1 in 50,000 to 1 in 117,000. The causative gene for Fabry disease is GLA located to chromosome Xq22. The loss of enzymatic activity leads to the systemic deposition of glycosphingolipid substrates in a number of cell types in the heart, kidney, eyes and other tissues. Death usually occurs from renal failure or cardiac/cerebrovascular disease.

Because of the monogenic nature of LSDs, enzyme replacement therapy (ERT) has become the first line of treatment for a number of LSDs, using purified recombinant enzymes to replace the defective enzymes in the lysosome and therefore reducing pathological substrate accumulation in the lysosome. Imiglucerase, taliglucerase and velaglucerase have been used for treating Gaucher disease; alglucosidase alfa for Pompe disease and agalsidase alfa/beta for Fabry disease (Desnick and Schuchman 2012; Parenti, Andria, and Valenzano 2015). ERT is administrated through direct intravenous infusion of recombinant enzymes to patients with inherited deficiencies. Even though it has been shown to successfully treat certain LSDs, it has limitations. First, it requires life-time intravenous infusion every 2 weeks, posing a high cost for treatment. Second, the tissue penetration of the enzymes varies among organs, with low penetration to the bones, lung and brain. Third, the efficacy of ERT is often reduced due to the unwanted immune response against the enzyme. Due to these drawbacks of ERT, substrate reduction therapy (SRT) using small molecules (Platt et al. 1994; Patterson et al. 2007; Lukina et al. 2010) or small interfering RNAs (Canals et al. 2015) has emerged as a second line of therapy for LSDs. SRT does not target the mutant enzyme; instead, it prevents/reduces the synthesis of substrates using small molecules to inhibit key enzymes in substrate biosynthesis pathways. It is a non-disease-specific LSD therapy, as all GSLs except galactosylceramide are synthesized through a common biosynthetic pathway with GCS as a rate limiting enzyme. This GCS synthase is the target for two currently approved drugs for treating a number of LSDs: miglustat (Machaczka et al.

2012) (Zavesca; Actelion Pharmaceuticals) and eliglustat (Lukina et al. 2010) (Cerdelga; Genzyme).

Miglustat was the first oral small molecule therapeutic drug approved by FDA in 2003 for treating moderate type 1 Gaucher disease that is not suitable for ERT. It is an imino sugar drug with glucose stereochemistry that acts as a GCS inhibitor. However, its serious side effects such as pain, burning, neurological, vision and gastrointestinal discomfort limits its clinical use (Remenova et al. 2015). Eliglustat, a recently approved small molecule by FDA in 2014 has become a first-line oral therapy for type 1 Gaucher disease. It is a stronger GCS inhibitor with equivalent efficacy to ERT and less severe side effects. However, it is also a substrate for CYP2D6, therefore requiring individual adaptation of the dose to be effective. In addition, Eliglustat inhibition carries impact on hundreds of different glycoproteins, leading to high cardiac adverse effect incident and increased risk of arrhythmia. Eliglustat has poor penetration across the blood-brain barrier, making it unsuitable for treating CNS related neurological disorders in GSL storage diseases (Mistry et al. 2015). Therefore, there is an urgent and growing need to develop better inhibitors for SRT. ibiglustat (Venglustat; Genz-682452; GZ/SAR402671), a potent and selective GCS inhibitor, showes great potential in complement and augment ERT therapies (Ashe et al. 2015; Marshall et al. 2016). It has low toxicity and is capable of traversing the blood-brain barrier, leading to improved clinical effectiveness with reduced side effects. Currently, ibiglustat is in phase II trials for Fabry, Gaucher and Parkinson diseases.

To this end, structural modification of existing drugs or potential drug-able small molecules has been playing a significant role in generating new chemical entities that are biologically potent and physiologically active with improved pharmacokinetic, therapeutic, and toxicological profiles. One such methodology that has been attempted is to use deuteration substitution as a tool for optimization of drug metabolic profiles and reduce toxicity (Harbeson et al. 2017; Timmins 2014; Russak and Bednarczyk 2018).

BRIEF SUMMARY OF INVENTION

The invention generally relates to therapeutics and treatment methods for certain diseases and conditions. Specifically, this invention provides novel chemical compounds, including [(3S)-1-azabicyclo[2.2.2]octan-3-yl]N-[2-[2-(4-fluorophenyl)-1,3-thiazol-4-yl]propan-2-yl]carbamate (also named ibiglustat) with one or more deuterium-substitutions at strategic positions, that are glucosylceramide synthase inhibitors and are useful for treating various types of lysosomal storage diseases including Fabry's disease, Gaucher's disease and Parkinson's disease, or related diseases and conditions, pharmaceutical compositions, and methods of preparation and use thereof.

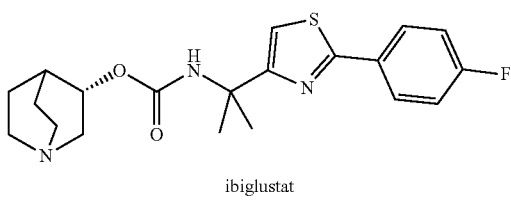 [SMILES: CC(C)(NC(=O)O[C@@H]1CN2CCC1CC2)c1csc(-c2ccc(F)cc2)n1]

ibiglustat

The compounds disclosed herein are modified versions of ibiglustat, wherein one or more hydrogen atoms are substituted with a deuterium atom at strategic locations. These compounds are potent and selective GCS inhibitors, and show great potential in complement and augment therapy with ERT. They have lower toxicity and are capable of traversing the blood-brain barrier, leading to improved clinical effectiveness with reduced side effects. The inventive compounds of the present invention are represented by the following Formula (I):

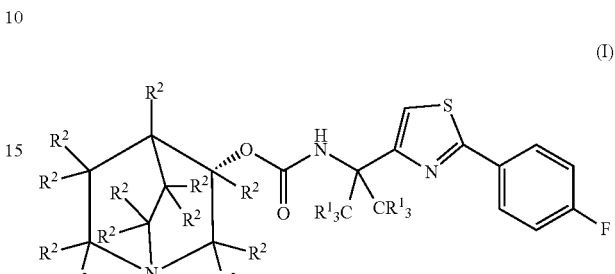

wherein each of $R^1$ and $R^2$ is independently selected from H, or D, and at least one of $R^1$ and $R^2$ is D.

In another aspect, the invention generally relates to a pharmaceutical composition comprising a compound of the Formula (I) or a pharmaceutically acceptable salt or ester thereof, that is a potent and selective GCS inhibitor and shows great potential in complement and augment therapy with ERT.

In another aspect, the invention generally relates to a dosage form comprising a compound of the Formula (I), wherein the dosage form is suitable for administrating to a subject, animal or human, that suffers from Fabry's disease, Gaucher's disease and Parkinson's disease, or related diseases and conditions.

In another aspect, the invention generally relates to a method of producing or using a compound of the Formula (I).

The foregoing has outlined rather broadly the features and technical advantages of the invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description. It is to be expressly understood, however, that any description, figure, example, etc. is provided for the purpose of illustration and description only and is by no means intended to define the limits of the invention.

BRIEF DESCRIPTION OF THE DRAWINGS

FIG. 1a. Mass spectrometric analysis of ibiglustat: Full-scan spectrum.

FIG. 1b. Mass spectrometric analysis of ibiglustat: Product-ion scan spectrum.

FIG. 2a. Mass spectrometric analysis of compound 1 (ibiglustat-d6): Full-scan spectrum.

FIG. 2b. Mass spectrometric analysis of compound 1 (ibiglustat-d6): Product-ion scan spectrum.

FIG. 3a. Mass spectrometric analysis of compound 1b (ibiglustat-d12): Full-scan spectrum.

FIG. 3b. Mass spectrometric analysis of compound 1b (ibiglustat-d12): Product-ion scan spectrum.

FIG. 4a. Mass spectrometric analysis of compound 1a (ibiglustat-d18): Full-scan spectrum.

FIG. 4b. Mass spectrometric analysis of compound 1a (ibiglustat-d18): Product-ion scan spectrum.

FIG. 5. Exemplary NMR spectrum of compounds of the invention (compound 1, ibiglustat-d6).

FIG. 6. Exemplary NMR spectrum of compounds of the invention (compound 1a, ibiglustat-d18).

FIG. 7. Exemplary NMR spectrum of compounds of the invention (compound 1b, ibiglustat-d12).

FIG. 8. Exemplary results of ibiglustat vs. compounds of the invention when co-incubated in rat microsomes.

FIG. 9. Exemplary results of ibiglustat vs. compounds of the invention when co-incubated in dog microsomes.

DETAILED DESCRIPTION OF THE INVENTION

I. Definitions

Unless otherwise noted, technical terms are used according to conventional usage.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The term "subject" refers to any animal (e.g., a mammal), including non-human primates, rodents, and the like, which is to be the recipient of a particular treatment. Typically, the terms "subject" and "patient" are used interchangeably herein in reference to a human subject.

The term "effective" as used in connection with an amount of an active agent, refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

The terms "treating, reducing, or preventing" a condition refer to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

The term "pharmaceutically acceptable excipient, carrier, or diluent", as used herein, refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; dextrin and cyclodextrin (alpha, beta and gamma); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

II. The Present Invention

The invention provides novel chemical compounds that may be used to treat lysosomal storage diseases (e.g., Gaucher, Fabry diseases). These compounds are biochemically potent and physiologically active, with improved pharmacokinetic, therapeutic and toxicological properties over ibiglustat. For comparison, ibiglustat was synthesized, tested and analyzed parallel to the compounds described in this invention. The mass spectrometric analytical results of ibiglustat are demonstrated in FIG. 1, showing an m/z value of 390 for ibiglust (FIG. 1a) and its gas-phase fragmentation pattern (FIG. 1b).

The compounds disclosed herein are deuterium-substituted versions of ibiglustat, where one or more hydrogen atoms are substituted with deuterium at strategic locations of the molecule. Three examples of such substitutions are shown in FIGS. 2-4. Such strategic deuterium substitution leads to positive impact on the pharmacokinetic, therapeutic and toxicological profiles of select compounds. The compounds disclosed herein are GSC inhibitors. The substitution locations are selected with the specific objective to impact pharmacokinetic, therapeutic, and toxicological properties of the molecule. The resulting compounds have 1 to 18 deuterium substitutions and exhibit more desirable metabolic and pharmacological profiles in terms of safety, efficacy and tolerability in the treatment of Fabry or Gaucher diseases and other related diseases including Parkinson's disease.

First-generation GCS inhibitor miglustat was approved by the FDA in 2003 to treat type I Gaucher disease when ERT was not an option and later for treating Niemann-Pick disease type C, another rare neurodegenerative, autosomal recessive lipid storage disease with mutations in the NPC1 gene that is involved in intracellular lipid trafficking (Platt, Boland, and van der Spoel 2012; Madra and Sturley 2010;

Rosenbaum and Maxfield 2011). It is a small water soluble iminosugar molecule derived from the naturally occurring glucosidase inhibitor deoxynojirimycin (Lachmann and Platt 2001; Platt et al. 1994) that reversibly inhibits glycosphingolipid synthesis (GCS). Patients with type 1 Gaucher disease normally show good initial responses to oral Miglustat treatment with improved biochemical outcomes, and lowered spleen and liver volumes (Cox et al. 2000; Heitner et al. 2002). Most patients who respond to therapy, however, suffered severe diarrhea and weight loss in about 6 to 12 months of treatment. Side effects have also been identified including neurological symptoms, and reproduction toxicity. Thus, its less favorable efficacy, safety and tolerability profile limit its clinical usage ((Cox et al. 2012); (http://www.ema.europa.eu/docs/en_GB/document_library/EPAR_-_product_information/human/000435/WC500046726.pdf (2013)).

Two-thirds of lysosomal storage disorders are accompanied with progressive neurological manifestations. Traditional enzyme replacement therapy failed to improve those neurological complications due to the blood-brain barrier. Miglustat did not show much improvement on this aspect as well. Second generation GSC inhibitor Eliglustat has been approved by FDA in 2017 as a first-line oral drug for treating adult type 1 Gaucher disease. It is a selective, more potent, enzyme-specific small molecular inhibitor of GCS (McEachern et al. 2007). Oral eliglustat is as effective as ERT in treating Gaucher disease (Cox et al. 2015; Mistry et al. 2015). Compared with miglustat, eliglustat showed stronger inhibitory potency (IC50=0.024 uM for eliglustat, IC50=5-50 uM for miglustat) and less gastrointestinal manifestation side effect because eliglustat does not inhibit intestinal enzyme (Smid et al. 2016; Balwani et al. 2016). However, it does not traverse the blood brain barrier (Shayman 2013), limiting its usage in treating neuronopoathic forms of Gaucher disease or other LSDs.

Therefore, current substrate reduction therapies for LSDs are quite limited. A significant unmet medical need exists for treating LSDs with neurological disorders. To this end, Sanofi-Genzyme has developed a promising novel GCS antagonist, ibiglustat, for the treatment of Fabry, Gaucher and other lipid storage diseases. Ibiglustat is a selective and potent GCS inhibitor with central nervous system (CNS) access (Ashe et al. 2015; Marshall et al. 2016), leading to improved clinical effectiveness with reduced side effects.

Compared to ibiglustat, the compounds disclosed herein are potent, selective inhibitors of GCS that show increased pharmacokinetic profiles. FIGS. 8 and 9 compare the in vitro metabolic profiles of ibiglustat vs. the compounds disclosed herein. Experimental results demonstrated that the compounds of the present invention showed increased stability over ibiglustat when they were 1:1 co-incubated in indicated pooled microsomes.

In addition to use as a monogenic SRT therapy, compounds of this invention may also be used in combination with ERT, that may confer both complementary and additive therapeutic benefits in lipid storage diseases including Fabry disease, Gaucher diseases.

In the present invention, all compounds disclosed herein have the general structure of Formula (I):

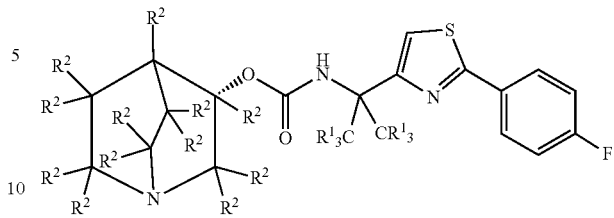

(I)

wherein each of $R^1$ and $R^2$ is independently selected from H, or D, and at least one of $R^1$ and $R^2$ is D.

In another aspect, the invention relates to a pharmaceutical composition comprising a compound of the Formula (I), or a pharmaceutically acceptable salt or ester thereof, effective to treat Fabry or Gaucher diseases and other related diseases including Parkinson's disease.

In another aspect, the invention relates to a dosage form comprising a compound of the Formula (I), wherein the dosage form is suitable for administrating to a subject, animal or human, that suffers from Fabry or Gaucher diseases and other related diseases including Parkinson's disease.

In another aspect, the invention relates to a method of making or using a compound of the Formula (I).

In certain embodiments, each of $R^1$ in the compound is D and each of $R^2$ is H, having the structural Formula (II) (ibiglustat-d6). The mass spectrometric analytical results of ibiglustat-d6 are demonstrated in FIG. 2, showing an m/z value of 396 (FIG. 2a) and the gas-phase fragmentation pattern (FIG. 2b).

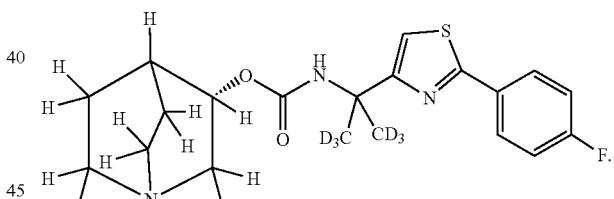

(II)

In another aspect, the invention relates to a pharmaceutical composition comprising a compound of the Formula (II), or a pharmaceutically acceptable salt or ester thereof, effective to treat Fabry or Gaucher diseases and other related diseases including Parkinson's disease.

In another aspect, the invention relates to a dosage form comprising a compound of the Formula (II), wherein the dosage form is suitable for administrating to a subject, animal or human, that suffers from Fabry or Gaucher diseases and other related diseases including Parkinson's disease.

In another aspect, the invention relates to a method of making or using a compound of the Formula (II).

In certain embodiments, each of $R^2$ in the compound is D and each of $R^1$ is H, having the structural Formula (III) (ibiglustat-d12). The mass spectrometric analytical results of ibiglustat-d12 are demonstrated in FIG. 3, showing an m/z value of 402 (FIG. 3a) and the gas-phase fragmentation pattern (FIG. 3b).

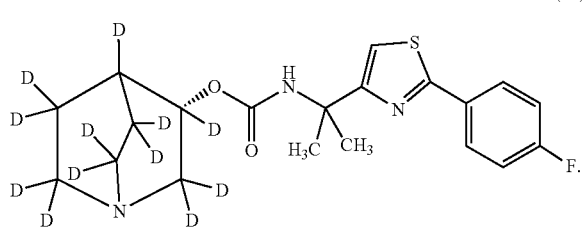

(III)

In another aspect, the invention relates to a pharmaceutical composition comprising a compound of the Formula (III), or a pharmaceutically acceptable salt or ester thereof, effective to treat Fabry or Gaucher diseases and other related diseases including Parkinson's disease.

In another aspect, the invention relates to a dosage form comprising a compound of the Formula (III), wherein the dosage form is suitable for administrating to a subject, animal or human, that suffers from Fabry or Gaucher diseases and other related diseases including Parkinson's disease.

In another aspect, the invention relates to a method of making or using a compound of the Formula (III).

In certain embodiments, each of $R^1$ and $R^2$ is D, having the structural formula (IV) (ibiglustat-d18). The mass spectrometric analytical results of ibiglustat-d18 are demonstrated in FIG. 4, showing an m/z value of 408 (FIG. 4a) and the gas-phase fragmentation pattern (FIG. 4b).

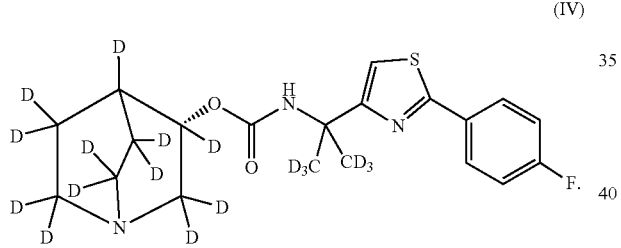

(IV)

In another aspect, the invention relates to a pharmaceutical composition comprising a compound of the Formula (IV), or a pharmaceutically acceptable salt or ester thereof, effective to treat Fabry or Gaucher diseases and other related diseases including Parkinson's disease.

In another aspect, the invention relates to a dosage form comprising a compound of the Formula (IV), wherein the dosage form is suitable for administrating to a subject, animal or human, that suffers from Fabry or Gaucher diseases and other related diseases including Parkinson's disease.

In another aspect, the invention relates to a method of making or using a compound of the Formula (IV).

In another aspect, the invention relates to a pharmaceutical composition comprising at least one compound selected from the group consisting of the compounds of Formulas (I) to (IV) or a pharmaceutically acceptable salt or ester thereof.

In yet another aspect, the invention relates to a unit dosage form comprising the pharmaceutical composition disclosed herein. The unit dosage is suitable for administration to a subject suffering Fabry or Gaucher diseases and other related diseases including Parkinson's disease.

In yet another aspect, the invention relates to a method for treating, reducing, or preventing a disease or disorder. The method includes: administering to a subject in need thereof a pharmaceutical composition comprising at least one compound selected from the group consisting of the compounds of Formulas (I) to (IV), or a pharmaceutically acceptable salt or ester thereof.

In certain preferred embodiments, the method of treatment includes administering to a subject in need thereof a pharmaceutical composition comprising a compound of any of the Formulas (I) to (IV), or a pharmaceutically acceptable salt or ester thereof.

IV. Examples

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described.

Example 1

Synthetic Scheme for the Synthesis of Compound 1

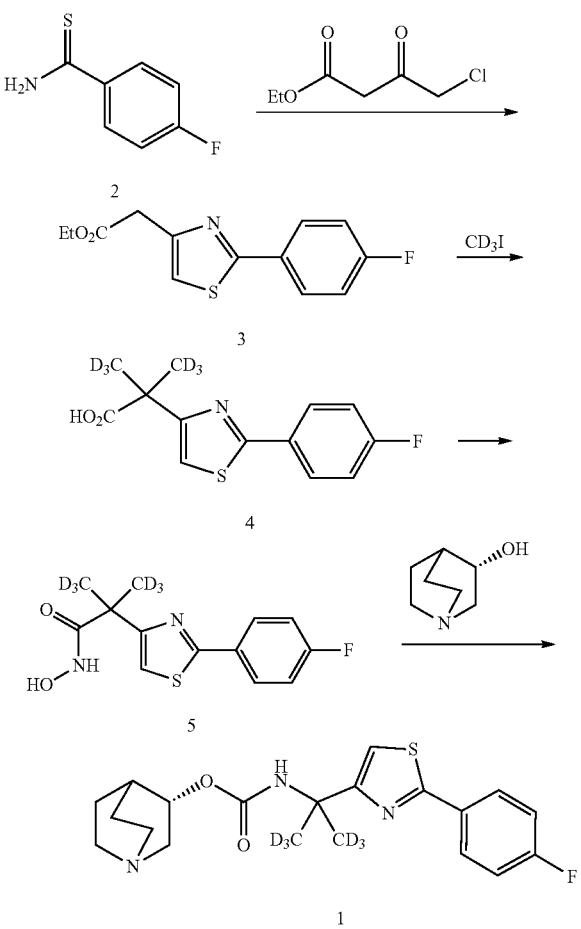

Synthesis of Compound 3

4-Fluorophenyl thioamide 2 (20 g, 128.9 mmol, 1 equiv) was dissolved in ethanol (100 mL) by heating to 50° C.

Ethyl 4-chloroacetoacetate (23.3 g, 141.8 mmol, 1.1 equivalent) was added dropwise. After 3 hours of reflux, the dark-brown solution was concentrated to dryness. To the residue, hexanes (100 mL) was added to get yellow solid. The solid was filtered and washed with hexanes (20 mL). The solid was subsequently neutralized with saturated bicarbonate aqueous solution (100 mL) and extracted with MTBE (100 mL×2). The combined organic layer was dried over $Na_2SO_4$ and concentrated to give compound 3 as a brown oil (25.8 g, 75% yield).

Synthesis of Compound 4

Compound 3 (8 g, 30.2 mmol, 1 equivalent) and $CD_3I$ (17.5 g, 120.6 mmol, 4 equivalent) were mixed in DMSO (60 mL). Cooled by ice bath, 50% NaOH aqueous solution (4.8 g, 120.6 mmol, 4 equivalent) was added dropwise. The mixture was stirred at room temperature overnight. The mixture was neutralized by 2 N HCl aqueous solution, then poured into water (150 mL) and extracted with MTBE (50 mL×3). The organic layer was dried over $Na_2SO_4$ and concentrated to give an oil (12.6 g). The residue was dissolved in THF (50 mL). A solution of lithium hydroxide monohydrate (3.6 g, 85.9 mmol) in water (50 mL) was added. The solution was heated at reflux overnight. The THF was removed on Rotavap to give a solution. The solution was extracted by MTBE (25 mL×2) and then acidified to pH=2-3 by 2 N HCl. The acidic aqueous solution with the gummy solid was extracted by MTBE (50 mL×3). The combined MTBE layer was dried over $Na_2SO_4$ and evaporated to get a solid. The solid was recrystallized by MTBE-hexanes (1:3, 75 mL) to afford an off-white solid 4 (5.1 g, yield 42%).

Synthesis of Compound 4a

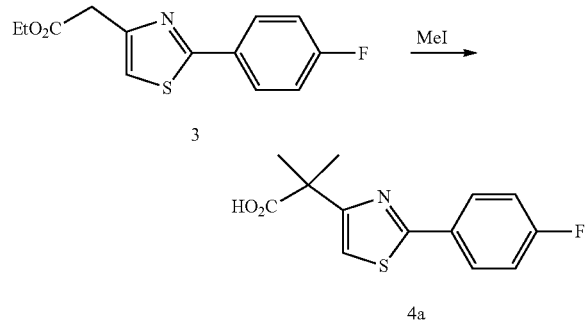

Repeat the synthetic procedure of compound 4 by using compound 3 and methyl iodide, to get compound 4a.

Synthesis of Compound 5

Compound 4 (3.0 g, 11.3 mmol, 1 equiv.) was dissolved in dry THF (20 mL) under nitrogen. Cooled by ice-bath, CDI (2.2 g, 13.5 mmol, 1.2 equivalent) was added. The ice-bath was removed, and the solution was stirred at room temperature for 1 h. The solution was again cooled in an ice-water bath, and hydroxylamine hydrochloride (1.6 g, 22.6 mmol, 2.0 equivalent) was added. The reaction mixture was stirred under nitrogen at room temperature overnight. The THF was then evaporated in vacuo and the residue was dissolved in ethyl acetate (50 mL). The ethyl acetate layer was washed with saturated bicarbonate solution (30 mL) and brine (30 mL) successively, dried over $Na_2SO_4$, and the solvent was evaporated in vacuo to obtain a pale-yellow solid. The solid was recrystallized with MTBE-hexane (4:1) to get compound 5 as an off-white solid (2.4 g, 76% yield).

Synthesis of Compound 5a

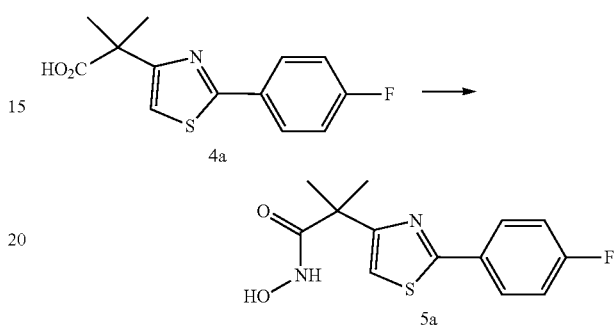

Repeat the synthetic procedure of compound 5 by using compound 4a, to get compound 5a.

Synthesis of Compound 1

To a stirred solution of compound 5 (0.64 g, 2.2 mmol, 1 equivalent) in MeCN (5 mL) at room temperature was added carbonyl diimidazole (0.42 g, 2.57 mmol, 1.15 equivalent). The reaction was stirred for 2 h and then concentrated to dryness. To the residue, toluene (10 mL) was added and the mixture was heated at reflux for 3 h. (S)-(+)-quinuclidinol (0.34 g, 2.67 mmol, 1.2 equivalent) was added and the reaction was heated at reflux for 16 hrs. The solution was cooled to room temperature and washed with water (10 mL). The aqueous phase was extracted with toluene (10 mL). The combined organic layer was washed with 1 N HCl (15 mL×2). The combined acidic aqueous layers were basified to pH=10-11 by 2 N NaOH. The formed gummy solid was extracted with DCM (15 mL×3). The DCM layer was washed with brine (20 mL), dried over $Na_2SO_4$ and concentrated to obtain a beige solid (0.53 g). The solid was recrystallized with MTBE to get compound 1 as an off-white solid (0.32 g, 45% yield).

Synthesis of Compound 1a

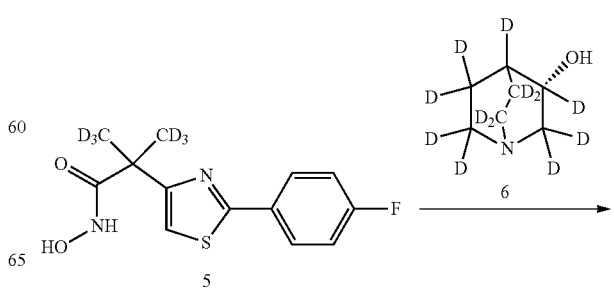

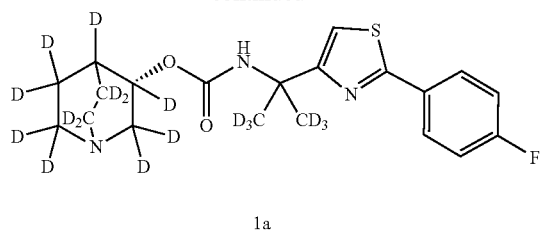

1a

Repeat the synthetic procedure of compound 1 by using compound 5 and compound 6, to get the compound 1a as off-white solid.

Synthesis of Compound 1b

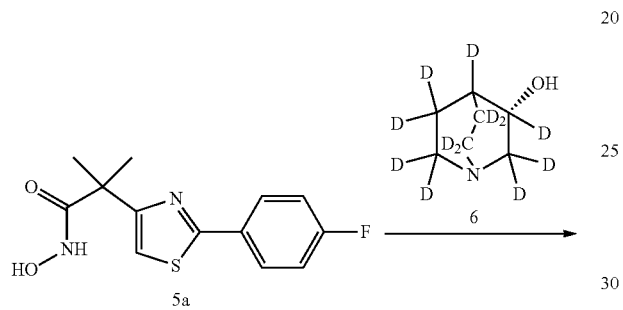

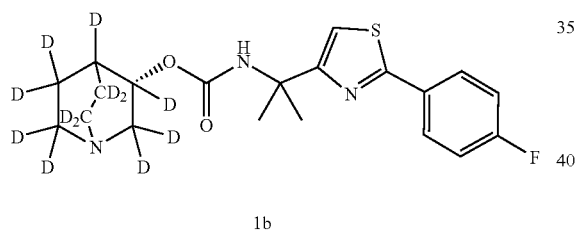

1b

Repeat the synthetic procedure of compound 1 by using compound 5a and compound 6, get the compound 1b as off-white solid.

Synthetic Scheme for the Synthesis of Compound 6

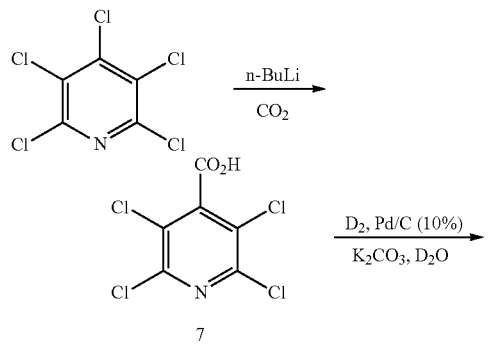

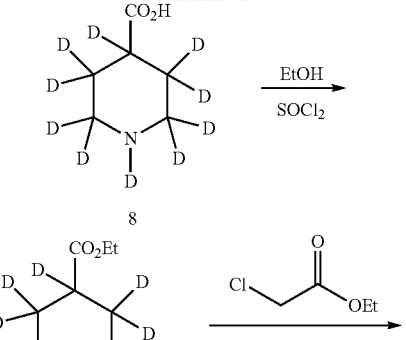

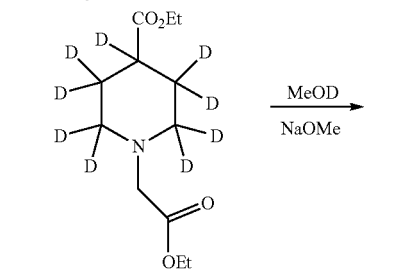

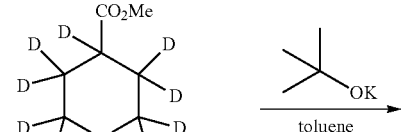

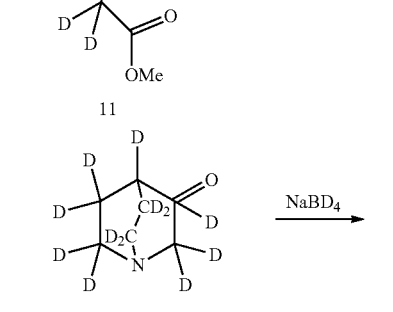

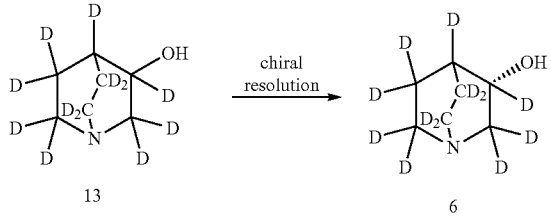

Synthetic Scheme for the Synthesis of Compound 7

To the pentachloropyridine (160 g, 0.63 mol, 1 equivalent) in ether solution (1.44 L) under $N_2$ below −55° C., n-BuLi (2.5 M in hexane. 270 mL, 1.06 equivalent) was added dropwise. The mixture was stirred below −55° C. for 30 min. Dry $CO_2$ was bubbled into the mixture and the temperature rose to room temperature. The mixture was acidified by adding conc. HCl (70 mL). The organic phase was separated and dried over $Na_2SO_4$, concentrated to dryness. The residue was suspended in refluxing DCM for 30 min, cooled down and filtered to get compound 7 as an off-white solid (80 g, 48% yield).

Synthesis of Compound 8

To a 1 L autoclave, compound 7 (38 g, 0.145 mol, 1 equiv) was mixed with 10% Pd/C (3.8 g) and $K_2CO_3$ (50.0 g, 0.362 mol, 2.5 equivalent in $D_2O$ (380 mL). After three nitrogen purges, the mixture was heated to 80° C. under $D_2$ (200 psi) for 24 hours. The mixture was filtered through a celite and was concentrated to dryness. The dryness was refluxing in toluene (200 mL) to remove the remaining $D_2O$ by Dean-Stark trap and the obtained solid 8 was directly used in the next step.

Synthesis of Compound 9

Compound 8 was suspended in EtOH (250 mL). Cooled by ice-bath, thionyl chloride (26.1 g, 0.22 mol) was added dropwise. The mixture was stirred at room temperature overnight and then heated and refluxed for 4 hours. The mixture was concentrated to give compound 9 and directly used in the next step.

Synthesis of Compound 10

Compound 9 was mixed with chloroacetate (27.8 g, 0.22 mol) in MeCN (150 mL). Cooled by ice-bath, $K_2CO_3$ (78.6 g, 0.57 mol) was added in portions. The mixture was stirred overnight and filtered through a celite pad. The filter cake was washed with MeCN (100 mL). The filtrate was concentrated to give compound 10 as a yellow oil (25.9 g, 71% yield from compound 7).

Synthesis of Compound 11

Compound 10 (14.8 g, 58.6 mmol, 1 equivalent) was refluxed with NaOMe (0.63 g, 11.7 mmol, 20% equiv) in MeOD (60 mL) for 20 hours. The mixture was concentrated to dryness. The residue was refluxed in MeOD (40 mL) for another 20 hours. After the solvent was evaporated, the residue was dissolved in DCM, washed with brine, dried over $Na_2SO_4$, and concentrated to give compound 11 as a yellow oil (12.2 g, 91% yield).

Synthesis of Compound 12

Potassium tert-butoxide (15.1 g, 134.8 mmol, 2.5 equivalent) was suspended in dry toluene (150 mL) and heated to reflux under $N_2$. Compound 11 (12.2 g, 53.9 mmol, 1 equivalent) in dry toluene (30 mL) was added dropwise to the above suspension. The mixture was kept refluxing for 3 hours and then cooled by ice-bath. DCl aqueous solution (30 g conc. DCl with 30 mL $D_2O$) was added to the reaction mixture. The aqueous phase was separated. The toluene phase was washed with diluted DCl (20 g conc. DCl with 10 mL $D_2O$). The combined aqueous phase was heated and refluxed for 18 hours. Cooled by ice-bath, the reaction solution was basified to pH=10-11 by $K_2CO_3$, extracted with DCM (80 mL×3). The DCM layer was dried over $Na_2SO_4$ and concentrated to give compound 12 as a yellow oil (4 g, 54% yield).

Synthesis of Compound 13

Compound 12 (4 g, 29.3 mmol, 1 equivalent) was dissolved in $D_2O$ (20 mL). Cooled by ice-bath, $NaBD_4$ (0.61 g, 14.6 mmol, 0.5 equivalent) was added to the solution. The mixture was stirred for 20 min at room temperature and then quenched by conc. DCl (2 g). The solution was basified by NaOH to pH=12-13 and concentrated to dryness. The residue was extracted with $CHCl_3$ (30 mL×2). The chloroform layer was dried over $Na_2SO_4$ and concentrated to give compound 13 as a yellow solid (3 g, 75% yield).

Chiral Resolution of Compound 13 to Obtain Compound 6

A mixture of dibenzoyl-L-(+)-tartaric acid monohydrate (4.4 g, 11.8 mmol), ethanol (20 mL) and racemic compound 13 (3 g, 23.6 mmol) was heated to reflux and maintained at reflux for 1 hour. After the solution was cooled to 0-5° C., the precipitating solid was filtered, washed with ethanol (10 mL), dried under vacuum to give a white solid (2.4 g). The obtained solid (2.4 g) was recrystallized three times in EtOH to give 1.6 g (S)-3-quinuclidinol dibenzoyl-L-(+)-tartrate salt. The salt was dissolved in water (5 mL). To the solution, 2 N HCl aqueous solution was added to get white solid. The solid was extracted with Ethyl acetate (15 mL). The EA layer was washed with water (3 mL). The combined aqueous layer was basified by NaOH to pH=12-13, extracted with chloroform (30 mL×3). The chloroform was dried over $Na_2SO_4$ and concentrated to give compound 6 as a white solid (0.3 g, yield 10%). The chiral purity of benzoylate of compound 6 was >99.5% ee.

NMR Analysis of Compounds 1, 1a and 1b

FIG. 5 shows the NMR spectrum of compound 1 (ibiglustat-d6). $^1$H NMR (400 MHz, $CDCl_3$): 7.94-7.90 (m, 2H), 7.13-7.07 (m, 3H), 5.56 (s, 1H), 4.69-4.67 (m, 1H), 3.23-3.18 (m, 1H), 2.84-2.59 (m, 4H), 2.0-1.76 (m, 5H).

FIG. 6 shows the NMR spectrum of compound 1a (ibiglustat-d18). $^1$H NMR (400 MHz, $CDCl_3$): 7.94-7.90 (m, 2H), 7.14-7.07 (m, 3H), 5.53 (s, 1H).

FIG. 7 shows the NMR spectrum of compound 1b (ibiglustat-d12). $^1$H NMR (400 MHz, $CDCl_3$): 7.94-7.90 (m, 2H), 7.14-7.07 (m, 3H), 5.53 (s, 1H), 1.76 (s, 6H).

Example 2

Incubation of Ibiglustat Verses Compounds of the Present Invention in Animal and Human Microsomes and in Vitro Sample Analysis by LC-MS/MS Reagents Dimethyl sulfoxide (DMSO) and acetonitrile (ACN) were obtained from VWR (Radnor, Pa.). 10×PBS buffer pH 7.4 was obtained from Thermo-Fischer Scientific (Waltham, Mass.). Ethylenediaminetetraacetic acid (EDTA) was obtained from Sigma-Aldrich (St. Louis, Mo.). Type I water was obtained from a reverse osmosis filtration system from MilliporeSigma (Burlington, Mass.). Dextromethorphan, ibiglustat, ibiglustat-d6, ibiglustat-d12, and ibiglustat-d18 were provided by Ascendex Scientific (Levittown, Pa.). Sodium hydroxide (NaOH) was obtained from Fisher Scientific (Hampton, N.H.). Human, beagle, rat and mouse microsomes, as well as NADPH regenerating system Solutions A and B, were obtained from Corning (Corning-Gentest, Tewksvury, Mass.).

Preparation of Primary Stock Solution and Working Solution

Each of the compounds presented in this disclosure (ibiglustat, ibiglustat-d6, ibiglustat-d12, and ibiglustat-d18) was weighed out in powder form and dissolved in DMSO to create primary stock solutions at concentrations of 10 mM. An aliquot of each primary solution was subsequently diluted in sample dilution buffer to a concentration of 100 µM. The four 100 µM solutions were then combined equally and diluted using sample dilution buffer to create a 4-in-1 solution in which each compound's concentration was 100 nM. Dextromethorphan was weighed out in powder form and dissolved in DMSO to create a primary stock solution with a concentration of 10 mM. The 10 mM stock was serially diluted in sample dilution buffer to create a working solution with a concentration of 100 nM. Each solution, upon dilution, was vortexed for at least two minutes to ensure homogeneity.

Preparation of Sample Dilution Buffer

To prepare 0.5 M EDTA (pH8.0) solution, disodium EDTA ($Na_2EDTA.2H_2O$) was dissolved in Type 1 water and pH to 8.0 was adjusted using sodium hydroxide. 1×PBS buffer (pH7.4) was prepared by diluting 10×PBS buffer pH 7.4 with Type 1 water. Sample dilution buffer was made by adding 1 mL of 0.5 M EDTA (pH8.0) solution to 99 mL of 1×PBS buffer pH 7.4.

Preparation of Microsome Solution

Rat and Dog pooled liver microsomes were purchased from Corning-Gentest (Tewksbury, Mass.) at a concentration of 20 mg protein/mL. They were diluted on ice to 5 mg/mL by combining three parts of 1×PBS with one part of 20 mg/mL microsome right before each experiment.

Preparation of Reaction Mixture

The reaction mixtures with or without microsomes were prepared as indicated in Table 1. As a negative control, microsome-free samples were prepared by substituting the microsome solution in the reaction mixture with an equal volume of 1×Phosphate Buffer Solution pH 7.4. The reaction mixture was prepared in triplicates. In addition, dextromethorphan was used in this assay as a positive control.

TABLE 1

Preparation of Reaction Mixture with or without Microsome

Preparation of Reaction Mixture of Sample with Microsome

| | |
|---|---|
| Test Compounds at 100 nM in Sample Dilution Buffer (25 nM final concentration during incubation) | 90 µL |
| Solution A | 13 µL |
| Solution B | 3 µL |
| 1× Phosphate Buffer Solution, pH 7.4 | 220 µL |
| 5 mg/mL Microsome Solution (1.25 mg/mL final concentration during incubation) | 34 µL |

Preparation of Reaction Mixture of Sample without Microsome

| | |
|---|---|
| Test Compounds at 100 nM in Sample Dilution Buffer (25 nM final concentration during incubation) | 90 µL |

TABLE 1-continued

Preparation of Reaction Mixture with or without Microsome

| | |
|---|---|
| Solution A | 13 µL |
| Solution B | 3 µL |
| 1× Phosphate Buffer Solution, pH 7.4 | 254 µL |

Incubation and Processing of Reaction Mixture

The reaction mixture was incubated in a water bath incubator at 37° C. At predetermined time points (0, 15, 30, 45, 60 and 120 minutes), an aliquot of 50 µL reaction mixture was removed from the incubation tube to a clean tube containing 250 µL of ice cold acetonitrile to terminate the reaction. The terminated aliquots were mixed well by vortexing and centrifuged for five minutes at 13,000 RPM. A portion of supernatant (~100 µL) was transferred to an autosampler vial and analyzed using liquid chromatography-mass spectrometry (LC-MS).

LC-MS/MS Analysis

Reversed-phase liquid chromatographic separation was done using ACE 3 C18 column (50×2.1 mm id, 3 µm). Mobile phase A was water with 0.1% formic acid and mobile phase B was acetonitrile with 0.1% formic acid with a combined flow rate of 0.3 mL/min. The applied gradient elution was: 10% B at 0 min, 90% B at 2 min, 90% B at 2.5 min, and 10% B at 2.6 min. Five compounds were monitored in positive mode over five-minute acquisition time by a triple quadrupole mass spectrometer. The sample run and data processing were done by Analyst version 1.6.2. Table 2 indicates multiple-reaction monitoring conditions of five analytes.

TABLE 2

MRM conditions of ibiglustat, ibiglustat-d6, ibiglustat-d12, ibiglustat-d18, and dextromethorphan

| Compounds | Q1 > Q3 (m/z) | DP | EP | CP | CXP |
|---|---|---|---|---|---|
| ibiglustat | 390.2 > 220.1 | 70 | 14 | 43 | 12 |
| ibiglustat-d6 | 396.4 > 226.1 | 90 | 10 | 45 | 12 |
| ibiglustat-d12 | 402.5 > 220.0 | 90 | 12 | 45 | 13 |
| ibiglustat-d18 | 408.5 > 226.0 | 90 | 11 | 45 | 11 |
| Dextromethorphan | 272.2 > 147.2 | 80 | 10 | 42 | 10 |

Results from Co-Incubation Studies

The compounds of the present invention showed higher stability over ibiglustat when they were 1:1 co-incubated in microsomes. As shown in FIGS. 8 and 9, deuterated ibiglustat showed increased stability in rat and dog microsomes.

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

REFERENCES

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure. The following is the list of references:

1. Ashe, K. M., E. Budman, D. S. Bangari, C. S. Siegel, J. B. Nietupski, B. Wang, R. J. Desnick, R. K. Scheule, J. P. Leonard, S. H. Cheng, and J. Marshall. 2015. 'Efficacy of Enzyme and Substrate Reduction Therapy with a Novel Antagonist of Glucosylceramide Synthase for Fabry Disease', *Mol Med*, 21: 389-99.
2. Balestrino, R., and A. H. V. Schapira. 2018. 'Glucocerebrosidase and Parkinson Disease: Molecular, Clinical, and Therapeutic Implications', *Neuroscientist*, 24: 540-59.
3. Balwani, M., T. A. Burrow, J. Charrow, O. Goker-Alpan, P. Kaplan, P. S. Kishnani, P. Mistry, J. Ruskin, and N. Weinreb. 2016. 'Recommendations for the use of eliglustat in the treatment of adults with Gaucher disease type 1 in the United States', *Mol Genet Metab*, 117: 95-103.
4. Canals, I., N. Beneto, M. Cozar, L. Vilageliu, and D. Grinberg. 2015. 'EXTL2 and EXTL3 inhibition with siRNAs as a promising substrate reduction therapy for Sanfilippo C syndrome', *Sci Rep*, 5: 13654.
5. Chan, B., and D. N. Adam. 2018. 'A Review of Fabry Disease', *Skin Therapy Lett*, 23: 4-6.
6. Cox, T., R. Lachmann, C. Hollak, J. Aerts, S. van Weely, M. Hrebicek, F. Platt, T. Butters, R. Dwek, C. Moyses, I. Gow, D. Elstein, and A. Zimran. 2000. 'Novel oral treatment of Gaucher's disease with N-butyldeoxynojirimycin (OGT 918) to decrease substrate biosynthesis', *Lancet*, 355: 1481-5.
7. Cox, T. M., D. Amato, C. E. Hollak, C. Luzy, M. Silkey, R. Giorgino, R. D. Steiner, and Group Miglustat Maintenance Study. 2012. 'Evaluation of miglustat as maintenance therapy after enzyme therapy in adults with stable type 1 Gaucher disease: a prospective, open-label non-inferiority study', *Orphanet J Rare Dis*, 7: 102.
8. Cox, T. M., G. Drelichman, R. Cravo, M. Balwani, T. A. Burrow, A. M. Martins, E. Lukina, B. Rosenbloom, L. Ross, J. Angell, and A. C. Puga. 2015. 'Eliglustat compared with imiglucerase in patients with Gaucher's disease type 1 stabilised on enzyme replacement therapy: a phase 3, randomised, open-label, non-inferiority trial', *Lancet*, 385: 2355-62.
9. de Camargo Pinto, L. L., S. W. Maluf, S. Leistner-Segal, C. Zimmer da Silva, A. Brusius-Facchin, M. G. Burin, S. Brustolin, J. Llerena, L. Moraes, L. Vedolin, A. Schuch, R. Giugliani, and I. V. Schwartz. 2011. 'Are MPS II heterozygotes actually asymptomatic? A study based on clinical and biochemical data, X-inactivation analysis and imaging evaluations', *Am J Med Genet A*, 155A: 50-7.
10. Desnick, R. J., R. Brady, J. Barranger, A. J. Collins, D. P. Germain, M. Goldman, G. Grabowski, S. Packman, and W. R. Wilcox. 2003. 'Fabry disease, an under-recognized multisystemic disorder: expert recommendations for diagnosis, management, and enzyme replacement therapy', *Ann Intern Med*, 138: 338-46.
11. Desnick, R. J., and E. H. Schuchman. 2012. 'Enzyme replacement therapy for lysosomal diseases: lessons from 20 years of experience and remaining challenges', *Annu Rev Genomics Hum Genet*, 13: 307-35.
12. Gault, C. R., L. M. Obeid, and Y. A. Hannun. 2010. 'An overview of sphingolipid metabolism: from synthesis to breakdown', *Adv Exp Med Biol*, 688: 1-23.
13. Harbeson, S. L., A. J. Morgan, J. F. Liu, A. M. Aslanian, S. Nguyen, G. W. Bridson, C. L. Brummel, L. Wu, R. D. Tung, L. Pilja, V. Braman, and V. Uttamsingh. 2017. 'Altering Metabolic Profiles of Drugs by Precision Deuteration 2: Discovery of a Deuterated Analog of Ivacaftor with Differentiated Pharmacokinetics for Clinical Development', *J Pharmacol Exp Ther*, 362: 359-67.
14. Heitner, R., D. Elstein, J. Aerts, Sv Weely, and A. Zimran. 2002. 'Low-dose N-butyldeoxynojirimycin (OGT 918) for type I Gaucher disease', *Blood Cells Mol Dis*, 28: 127-33.
15. Lachmann, R. H., and F. M. Platt. 2001. 'Substrate reduction therapy for glycosphingolipid storage disorders', *Expert Opin Investig Drugs*, 10: 455-66.
16. Lieberman, A. P., R. Puertollano, N. Raben, S. Slaugenhaupt, S. U. Walkley, and A. Ballabio. 2012. 'Autophagy in lysosomal storage disorders', *Autophagy*, 8: 719-30.
17. Lukina, E., N. Watman, E. A. Arreguin, M. Banikazemi, M. Dragosky, M. Iastrebner, H. Rosenbaum, M. Phillips, G. M. Pastores, D. I. Rosenthal, M. Kaper, T. Singh, A. C. Puga, P. L. Bonate, and M. J. Peterschmitt. 2010. 'A phase 2 study of eliglustat tartrate (Genz-112638), an oral substrate reduction therapy for Gaucher disease type 1', *Blood*, 116: 893-9.
18. Machaczka, M., R. Hast, I. Dahlman, R. Lerner, M. Klimkowska, M. Engvall, and H. Hagglund. 2012. 'Substrate reduction therapy with miglustat for type 1 Gaucher disease: a retrospective analysis from a single institution', *Ups J Med Sci*, 117: 28-34.
19. Madra, M., and S. L. Sturley. 2010. 'Niemann-Pick type C pathogenesis and treatment: from statins to sugars', *Clin Lipidol*, 5: 387-95.
20. Marshall, J., Y. Sun, D. S. Bangari, E. Budman, H. Park, J. B. Nietupski, A. Allaire, M. A. Cromwell, B. Wang, G. A. Grabowski, J. P. Leonard, and S. H. Cheng. 2016. 'CNS-accessible Inhibitor of Glucosylceramide Synthase for Substrate Reduction Therapy of Neuronopathic Gaucher Disease', *Mol Ther*, 24: 1019-29.
21. McEachern, K. A., J. Fung, S. Komarnitsky, C. S. Siegel, W. L. Chuang, E. Hutto, J. A. Shayman, G. A. Grabowski, J. M. Aerts, S. H. Cheng, D. P. Copeland, and J. Marshall. 2007. 'A specific and potent inhibitor of glucosylceramide synthase for substrate inhibition therapy of Gaucher disease', *Mol Genet Metab*, 91: 259-67.
22. Mistry, P. K., G. Lopez, R. Schiffmann, N. W. Barton, N. J. Weinreb, and E. Sidransky. 2017. 'Gaucher disease: Progress and ongoing challenges', *Mol Genet Metab*, 120: 8-21.
23. Mistry, P. K., E. Lukina, H. Ben Turkia, D. Amato, H. Baris, M. Dasouki, M. Ghosn, A. Mehta, S. Packman, G. Pastores, M. Petakov, S. Assouline, M. Balwani, S. Danda, E. Hadjiev, A. Ortega, S. Shankar, M. H. Solano, L. Ross, J. Angell, and M. J. Peterschmitt. 2015. 'Effect of oral eliglustat on splenomegaly in patients with Gaucher disease type 1: the ENGAGE randomized clinical trial', *JAMA*, 313: 695-706.
24. Parenti, G., G. Andria, and K. J. Valenzano. 2015. 'Pharmacological Chaperone Therapy: Preclinical Development, Clinical Translation, and Prospects for the Treatment of Lysosomal Storage Disorders', *Mol Ther,* 23: 1138-48.
25. Patterson, M. C., D. Vecchio, H. Prady, L. Abel, and J. E. Wraith. 2007. 'Miglustat for treatment of Niemann-Pick C disease: a randomised controlled study', *Lancet Neurol,* 6: 765-72.
26. Platt, F. M., B. Boland, and A. C. van der Spoel. 2012. 'The cell biology of disease: lysosomal storage disorders: the cellular impact of lysosomal dysfunction', *J Cell Biol,* 199: 723-34.
27. Platt, F. M., G. R. Neises, R. A. Dwek, and T. D. Butters. 1994. 'N-butyldeoxynojirimycin is a novel inhibitor of glycolipid biosynthesis', *J Biol Chem,* 269: 8362-5.
28. Remenova, T., O. Morand, D. Amato, H. Chadha-Boreham, S. Tsurutani, and T. Marquardt. 2015. 'A double-blind, randomized, placebo-controlled trial studying the effects of *Saccharomyces boulardii* on the gastrointestinal tolerability, safety, and pharmacokinetics of miglustat', *Orphanet J Rare Dis,* 10: 81.
29. Rosenbaum, A. I., and F. R. Maxfield. 2011. 'Niemann-Pick type C disease: molecular mechanisms and potential therapeutic approaches', *J Neurochem,* 116: 789-95.
30. Russak, E. M., and E. M. Bednarczyk. 2018. 'Impact of Deuterium Substitution on the Pharmacokinetics of Pharmaceuticals', *Ann Pharmacother:* 1060028018797110.
31. Saftig, P. 2006. 'Physiology of the lysosome.' in A. Mehta, M. Beck and G. Sunder-Plassmann (eds.), *Fabry Disease: Perspectives from 5 Years of FOS* (Oxford).
32. Schultz, M. L., L. Tecedor, M. Chang, and B. L. Davidson. 2011. 'Clarifying lysosomal storage diseases', *Trends Neurosci,* 34: 401-10.
33. Shayman, J. A. 2013. 'The design and clinical development of inhibitors of glycosphingolipid synthesis: will invention be the mother of necessity?', *Trans Am Clin Climatol Assoc,* 124: 46-60.
34. Smid, B. E., M. J. Ferraz, M. Verhoek, M. Mirzaian, P. Wisse, H. S. Overkleeft, C. E. Hollak, and J. M. Aerts. 2016. 'Biochemical response to substrate reduction therapy versus enzyme replacement therapy in Gaucher disease type 1 patients', *Orphanet J Rare Dis,* 11:28.
35. Timmins, G. S. 2014. 'Deuterated drugs: where are we now?', *Expert Opin Ther Pat,* 24: 1067-75.

What is claimed is:

1. A compound of the following Formula (II):

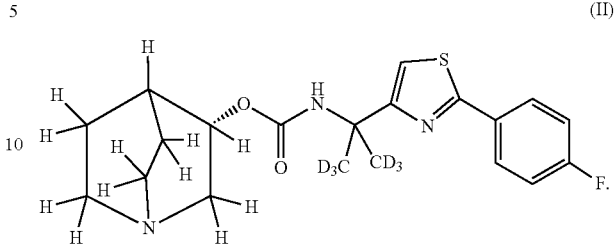

2. A compound of the following Formula (III):

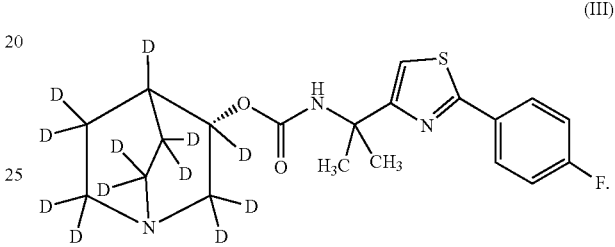

3. A compound of the following Formula (IV):

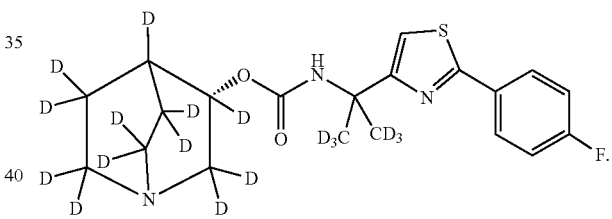

* * * * *